United States Patent
Pulkkinen et al.

(10) Patent No.: US 6,954,148 B2
(45) Date of Patent: Oct. 11, 2005

(54) METHOD AND SYSTEM FOR SELECTIVELY MONITORING ACTIVITIES IN A TRACKING ENVIRONMENT

(75) Inventors: Otto Pulkkinen, Helsinki (FI); Matti Häkkinen, Espoo (FI); Jukka-Pekka Särkkä, Espoo (FI)

(73) Assignee: Instrumentarium Corporation, Helsinki (FI)

( * ) Notice: Subject to any disclaimer, the term of this patent is extended or adjusted under 35 U.S.C. 154(b) by 127 days.

(21) Appl. No.: 10/444,538

(22) Filed: May 23, 2003

(65) Prior Publication Data

US 2003/0227386 A1 Dec. 11, 2003

Related U.S. Application Data

(60) Provisional application No. 60/386,475, filed on Jun. 6, 2002.

(51) Int. Cl.[7] .............................................. G08B 13/14
(52) U.S. Cl. ............................ 340/572.1; 340/573.4; 340/539.13
(58) Field of Search ........................ 340/572.1, 573.1, 340/573.4, 539.1, 539.12, 539.13

(56) References Cited

U.S. PATENT DOCUMENTS

| | | | |
|---|---|---|---|
| 4,225,953 A | 9/1980 | Simon et al. ................ 367/117 |
| 4,688,026 A | 8/1987 | Caracciolo et al. | |
| 4,857,716 A | 8/1989 | Hendrickson et al. | |
| 5,046,659 A | 9/1991 | Warburton ....................... 705/3 |
| 5,072,383 A | 12/1991 | Brimm et al. .......... 364/413.02 |
| 5,077,666 A | 12/1991 | Brimm et al. .......... 364/413.02 |
| 5,218,344 A * | 6/1993 | Ricketts .................... 340/573.4 |
| 5,301,353 A | 4/1994 | Borras et al. .................... 455/9 |
| 5,458,123 A | 10/1995 | Unger ......................... 128/696 |
| 5,561,412 A | 10/1996 | Novak et al. .......... 340/286.07 |
| 5,572,195 A | 11/1996 | Heller et al. ........... 340/825.35 |
| 5,583,758 A | 12/1996 | McIlroy et al. ............. 395/202 |
| 5,689,229 A * | 11/1997 | Chaco et al. .......... 340/286.07 |
| 5,713,350 A | 2/1998 | Ishimaro et al. | |
| 5,732,401 A | 3/1998 | Conway ....................... 705/29 |
| 5,740,800 A | 4/1998 | Hendrickson et al. ....... 128/630 |
| 5,748,907 A | 5/1998 | Crane .......................... 395/202 |
| 5,752,976 A | 5/1998 | Duffin et al. .................. 607/32 |
| 5,759,199 A | 6/1998 | Snell et al. .................... 607/60 |

(Continued)

FOREIGN PATENT DOCUMENTS

| | | |
|---|---|---|
| WO | WO 00/03344 A | 1/2000 |
| WO | WO 01/33748 | 2/2001 |

OTHER PUBLICATIONS

Axcess, Inc.—Web Site, 1998–2001 "AXCESS Asset Tagging and Integrated Digital Video in Healthcare", http://www.axsi.com.

Instantel, Inc.—Web Site Jun. 26, 2001 "Find It", http://www.instantel.com.

Versus Technology, Inc.—Web Site Jun. 26, 2001 "Versus Information System", http://www.versustech.com.

*Primary Examiner*—John Tweel, Jr.
(74) *Attorney, Agent, or Firm*—Norris, McLaughlin & Marcus (57) ABSTRACT

A system for selectively collecting location information in a tracking environment includes a first energy signal identification badge for detecting trigger signals and transmitting identification data signals indicating existence of a proximity condition between the first badge and a source of the trigger signals. The trigger source transmits trigger signals of a predetermined power level, wherein the first badge can detect the trigger signals only if the first badge is within a predetermined radius of the trigger source when the trigger source transmits the trigger signals. The first badge transmits the identification data signals when the first badge detects the trigger signals transmitted by the trigger source.

17 Claims, 3 Drawing Sheets

U.S. PATENT DOCUMENTS

| | | | | |
|---|---|---|---|---|
| 5,785,530 A | | 7/1998 | Smith | 434/219 |
| 5,822,544 A | | 10/1998 | Vincens et al. | |
| 5,877,675 A | | 3/1999 | Rebstock et al. | 340/286.07 |
| 5,953,704 A | | 9/1999 | McIlroy et al. | 705/2 |
| 5,960,085 A | | 9/1999 | de la Huerga | 380/25 |
| 5,991,730 A | | 11/1999 | Lubin et al. | 705/3 |
| 6,080,106 A | * | 6/2000 | Lloyd et al. | 600/300 |
| 6,104,295 A | | 8/2000 | Gaisser et al. | 340/573.4 |
| 6,154,139 A | | 11/2000 | Heller | 340/573.4 |
| 6,211,790 B1 | | 4/2001 | Radomsky et al. | 340/573.4 |
| 6,230,142 B1 | | 5/2001 | Benigno et al. | 705/3 |
| 6,259,355 B1 | | 7/2001 | Chaco et al. | 340/286.07 |
| 6,346,886 B1 | * | 2/2002 | De La Huerga | 340/573.1 |
| 6,373,389 B1 | * | 4/2002 | Przygoda et al. | 340/572.4 |
| 6,539,393 B1 | * | 3/2003 | Kabala | 707/102 |
| 6,727,810 B1 | * | 4/2004 | Martin et al. | 340/506 |
| 6,747,561 B1 | * | 6/2004 | Reeves | 340/573.1 |
| 6,788,199 B2 | * | 9/2004 | Crabtree et al. | 340/539.13 |

* cited by examiner

METHOD AND SYSTEM FOR SELECTIVELY MONITORING ACTIVITIES IN A TRACKING ENVIRONMENT

This is a nonprovisional application claiming priority of provisional application No. 60/386,475, filed Jun. 6, 2002.

FIELD OF THE INVENTION

The present invention relates generally to a method and system for monitoring activities in a tracking environment and, more particularly, a method and system for collecting activity data from within a tracking environment and processing the collected activity data to make information concerning monitored activities and status of an event schedule available in real time. Further still, the invention relates to a system which allows for tracking of personnel, on a selective basis, responsive to trigger signals or situations, in order to preserve privacy of the tracked individual.

BACKGROUND OF THE INVENTION

In a hospital, the ability to monitor activities relating to operational processes, such as scheduling patient flow through a diagnostic or treatment room, and the performance of events associated with patient medical treatment is important. By accurately and completely monitoring such activities, actions can be taken to ensure that appropriate health care steps are being performed properly and within the required time frame. Also, the movement of patients and caregivers, interaction between patients and caregivers and the health care steps taken with respect to a patient can be better managed and tracked.

If monitoring of activities must be performed manually, such as having a person type information into a terminal, the desired monitoring likely will not be achieved. A caregiver may not remember or input the actual time an event occurred when the caregiver enters the information manually. If a record of patient medical treatment activities is not accurate, selected medical treatment events likely will not be performed in proper sequence in relation with other medical treatment events, thereby precluding comparison and evaluation of medical treatment events in a rapidly changing care environment.

In acute care in a hospital, the activities performed by or associated with the medical treatment provided by a caregiver having clinical expertise and also a competency in operational and business functions, known as a clinical-operational hybrid caregiver, lend themselves to monitoring. Such hybrid caregivers include, for example, a clinical nurse specialist who has a masters preparation in nursing, is a clinical expert in the application of evidence-based practice and is responsible to senior hospital leadership to achieve quality, cost-effective patient outcome for a high volume patient population, which is typically defined by diagnoses such as stroke, congestive heart failure, respiratory failure, myocardial infarction and pneumonia. Other clinical-operational hybrid caregivers can include unit based case managers, discharge planners, hospitalists, intensivists and chief medical officers. It has been recognized that if the activities performed by or associated with the hybrid caregiver are monitored accurately and completely, the medical treatment related information collected can be used by the hybrid caregiver, as well as others, to establish performance measures and goals across clinical, financial, growth, and patient satisfaction perspectives.

In addition, by monitoring the medical treatment provided to a patient, the progression of medical treatment relating to a patient care schedule, which usually follows clinical practice care guidelines, can be better assessed. A patient care schedule essentially constitutes a schedule of events for a patient which is defined based on medical treatment guidelines developed by various professional practice, caregiver and hospital associations. The guidelines are usually based on the best evidence available on prevention, diagnosis, prognosis, therapy, avoidance of harm, e.g. negative side effects, and cost-effectiveness. One form of a patient schedule, known as a clinical care pathway, has been found to aid clinicians in decision-making by defining practice questions and identifying decision options and likely outcomes. The schedule of events for a care pathway can address, for example, specific health problems or diagnoses and require the collection of the following clinical information: patient name and arrival time; assessment of patient condition, such as by diagnosis, time and caregiver; tests to be performed and already completed and at what respective times; test results received and at what times; times and descriptions of planned and performed interventions by caregivers; re-assessment(s) of patient condition indexed by indicated diagnosis, time and caregiver; and time of discharge or transfer. It has been found that consideration of a caregiver's clinical judgment and a patient's values and expectations, while providing medical treatment for patients in accordance with a patient schedule, results in improved and cost effective care outcomes.

A further benefit of accurate and complete monitoring of activities related to medical treatment and operational processes is that the risk and cost of litigation relating to health care can be reduced. A permanent, irrefutable record of events that occurred is established, such that a question as to what events indeed occurred no longer exists and can be raised.

In addition, accurate and complete monitoring of medical treatment and operational process activities can help, and in some circumstances is necessary, to satisfy regulatory requirements. Standards presently in place and which are being developed require hospitals to initiate efforts to improve, for example, clinical performance. These data-driven performance measures are a factor in the accreditation process and provide for standardization of measurements between hospitals, thereby enabling benchmarking within and between hospitals. The clinical measures that need to be monitored for regulatory purposes include those that (i) are designed to evaluate the processes or outcomes of care associated with the delivery of clinical services; (ii) allow for intra- and inter-organizational comparisons to be used to continuously improve patient health outcomes; (iii) allow for focus on the appropriateness of clinical decision making and implementation of these decisions; and (iv) address important functions of patient health care, for example, medication use, infection control, patient assessment, etc.

Also, accurate and complete monitoring of activities associated with the sequence of medical treatment and operational process events that occur in relation to patient health care can make allocation of resources, personnel and equipment more efficient.

Therefore, a strong desire and need exists to incorporate and integrate one or more of the following features or functions into a comprehensive monitoring system: collecting accurate, complete and irrefutable data representative of monitored activities relating to medical treatment and operational processes; determining progress on a patient care schedule; meeting regulatory requirements; reducing the risk of litigation; establishing a real time accessible record of events that have occurred, including caregiver and patient locations indexed by time; tracking and modeling resource utilization; tracking the performance of caregivers; and reducing documentation burden upon caregivers.

Although systems which rely on logistics to collect and process activity data exist in industries such as warehousing and distribution, a comprehensive system for monitoring human tasks and interaction with monitored patients in a tracking environment, and which specifically addresses the needs of an acute health care facility, is not available.

Moreover, current techniques for monitoring activities in a health care facility are not completely satisfactory because they do not permit accurate, real time and substantially complete collection of the health care information from which real time assessments on the progress of health care for patients can be performed. U.S. Pat. No. 5,991,730, incorporated by reference herein, for example, discloses a patient tracking technique which tracks patient location by detecting movement of the patient medical file among receptacles located at a medical facility. The information collected and relied upon to make the location determination constitutes low level information which does not permit a real time health care assessment.

Similarly, while there are many known techniques that provide for the management and documentation of information related to patient schedules, such techniques do not include the feature of real time assessment of the collected information in connection with medical treatment guidelines. For example, U.S. Pat. No. 6,230,142, incorporated by reference herein, describes a system that enables a caregiver to store and analyze clinical pathway data, to make historical comparisons, such as identifying trends in the data, and to provide after-the-fact health care outcome tracking and documentation capabilities. In addition, U.S. Pat. Nos. 5,953,704 and 5,583,758, incorporated by reference herein, disclose systems which caregivers utilize offline to perform comparisons between proposed and actual care paths and their outcomes. Also, U.S. Pat. No. 5,740,800, incorporated by reference herein, describes an information system for clinical pathway management which, based on caregiver input, assists in the selection of correct order sets for care patients. U.S. Pat. No. 5,785,530, incorporated by reference herein, discloses a system used for three-dimensional visualization of clinical pathways. The above-mentioned patents, while providing for processing of collected clinical care information, do not include the feature of using the collected information to assess the progress of medical treatment in relation to patient schedule criteria in real time.

U.S. Pat. No. 5,960,085 describes a system that permits a patient or a caregiver to access confidential patient information upon detection of an electronic identification card by a computer system. This system, while enhancing secure data access, similarly does not contemplate or describe the use of the collected information to assess the progress of health care in real time.

A comprehensive health care facility management system is currently available from Versus Technology, Inc. The system employs IR/RF technology to provide real-time, continuous, location-specific information about people and equipment as they move through the facility. Each person or piece of equipment wears a transmitting badge with a unique ID. Data is collected passively, to provide information on room status, equipment being utilized for a given patient, and presence and frequency of interaction between patient and staff.

Patient movement is facilitated by directing patients to available testing areas. Instant knowledge of the onset and duration of a procedure allows the facility to plan ahead. The amount of time spent between a patient and a caregiver is recorded, as the amount of time for a particular procedure. The data is used for reports, particularly those for compliance with JCAHO standards. Some of the reports available include a Tracking Log, which details the movement of an individual or piece of equipment throughout the facility, including identifying each room entered, arrival and departure time and total time spent in each room. A Time Together report shows how much time different people or equipment have spent together in a particular room for any given time period. This data may be used for billing or audit reports. Although the mechanism of the time together report is not set out, it appears that it searches for same-room presence during a common time frame for two people/equipment, rather than recording a direct proximity signal between the two <http://www.versustech.com>.

Linked interaction between two objects, for example a person and equipment within a health care facility is taught by Axcess Inc. Using RFID tagging technology, a system provides for tracking and location assets throughout a facility on-demand, determining equipment status and inventory, locating personnel, protecting assets from unauthorized removal from a ward or facility. The latter is achieved by providing tags for each piece of equipment. As the equipment approaches an exit door or other restricted area, the tag is identified and appropriate alarm signal can be sent. Personnel tags can be linked via software to particular assets or a certain type of equipment, with a defined relationship permitting the free movement of the equipment only when it is accompanied by an authorized person. The system is programmed to override the alarm signal when the identified location of a piece of equipment and an authorized person coincide. <http://www.axsi.com/whitepapers/wp health.shtml>.

U.S. Pat. No. 6,154,139 relates to a method and system for locating subjects within a tracking environment, such as a health care facility. Personnel (such as patients and caregivers) are provided with transmitting tags, which transmit both an IR (line-of-sight) identifying signal and a RF (non-line-of-sight) identifying signal. The IR signal is effective in accurately determining location to a specific degree. However, because it requires line-of-sight, it can not be used to locate personnel in sensitive areas where IR receivers are not placed. In this case, a RF signal may reach a RF receiver within a certain distance, even through walls. Therefore, if a patient presses a distress call from the bathroom, the RF receiver transmits this signal to the central processor, which can locate the patient by way of the last IR signal received (e.g. hallway outside of bathroom).

U.S. Pat. No. 6,211,790 relates to an infant-parent matching system, based on a dual-mode infrared/radio frequency (IR/RF) transmitter secured within a wristband worn by the mother and within an ankle and/or wristband worn by the infant. In a matching mode of operation, IR signals are received by infrared receivers located within the various rooms of the hospital to precisely and automatically determine by proximity that mother and infant are correctly united. In a presence detecting mode, RF signals from the infant's badge are detected by RF receivers located throughout the maternity ward of the hospital or throughout the hospital generally. In a security mode, RF receivers located proximate exits of either of the maternity ward and/or the hospital detect RF signals from the ankle and provide a signal to generate an alarm.

Thus, there exists a need for an automated system which efficiently, accurately and without much, if any, human action monitors activities in a tracking environment in real time to create an accurate and automatic electronic historical record of events and patient-caregiver interactions, to permit real time assessment of the progress of patient health care.

Although continuous tracking of the locations of both patients and caregivers can be performed using infrared ("IR") and/or radio frequency ("RF") signal location and tracking technology, such as described in U.S. Pat. No. 6,154,139 and WO 01/33748, incorporated by reference herein, many caregivers are reluctant to be monitored continuously because they believe that continuous real time monitoring interferes with their privacy. Some monitoring systems that attempt to address the privacy concern rely exclusively upon line-of-sight IR signals-based location tracking technology to track the presence of caregivers only in selected locations. Such IR-based systems, however, operate within the known limitations of IR line-of-sight detection, which often does not provide accurate and complete location information concerning the person being tracked. Other current systems attempt to address the privacy concern of caregivers by monitoring only patients. These and other known approaches for addressing privacy concerns of caregivers decrease the overall value and usefulness of the collected activity data.

Although continuous tracking of both patients and caregivers can be performed using infrared ("IR") and/or radio frequency ("RF") signal location and tracking technology, such as described herein, simply locating both in the same logical care area is often not sufficient for positively identifying a meaningful interaction between them. For example, when a nurse visits a patient room occupied by several patients, it may be essential from the process monitoring point of view to determine which of the patients she or he is visiting. If the room is crowded and the patient beds are located in close proximity, typical location system installations are often not accurate enough to do this reliably. With some installations, an attempted solution to this problem has involved building a very dense infrared sensor network and limiting the zone tracked by an individual sensor small enough to cover a single bed. However, this kind of approach is typically very costly because of the large numbers of sensors and the installation work required if the sensor network is to be made ubiquitous. Furthermore, many caregivers are reluctant to be monitored continuously.

Therefore, there is a further need to collect activity data completely and accurately in a tracking environment without interfering with the privacy of the caregivers.

SUMMARY OF THE INVENTION

In accordance with the present invention, a method and system for monitoring activities within a tracking environment collects activity data, preferably in real time, and automatically processes the collected data in real time to assess end update the status of performance of a schedule of events, and to make information concerning the schedule status and the monitored activities available for real time and archival retrieval. In a preferred embodiment, the tracking environment is a health care facility; the monitored activities include medical treatment and operational process events, such as physiological measurements, patient and caregiver locations, patient, caregiver and medical equipment proximity information and evidence of interventions or actions between a caregiver and a particular patient; and the schedule is a patient care event schedule, such as a clinical care pathway, including medical treatment and operational process events which a caregiver selects for the patient.

In a preferred embodiment, the system includes a controller coupled by a wireless, wired or combination wired and wireless network to sensors, identification badges, physiological output data monitoring equipment and portable or fixed interfaces, each of which is located within a tracking environment. Each of the badges is either an active device, such as an IR or RF transceiver which automatically or upon manual triggering or detection of a trigger signal transmits encoded identification data signals, a passive device, such as an RF transponder or an IR readable barcode which when interrogated respectively by an RF or IR source reflects encoded identification data signals, or a combination active and passive device. The badges can be located or carried directly on or adjacent to patients, caregivers and fixed or portable diagnostic or medication dispensing equipment. The output monitoring equipment is coupled to medical diagnostic or treatment equipment, or to existing data networks to which the medical equipment may already be coupled. The monitoring equipment further includes a transmitter that transmits to the controller time encoded activity data signals representative of physiological conditions, such as vital signs, that the medical or diagnostic equipment measures, as well as the identities of the caregiver operating the medical equipment and the patient being monitored. The interfaces preferably include a graphical display, manual or voice data input capabilities and a transceiver apparatus which receives control signals from and transmits energy signals including activity data and other data, such as instructions for modifying a patient care schedule, manually input by a caregiver to the controller, preferably over a hardwired electrical or optical data signal communication link. The sensors are energy signal transceivers which detect IR and/or RF encoded identification data signals and transmit to the controller, also preferably over the hardwired link, digital activity data signals representative of the detected identification data signals. Preferably, the sensors are positioned at strategic, predetermined locations throughout a tracking environment to ensure complete and accurate monitoring. In a preferred embodiment, the collected activity data is representative of IR or RF energy signal interaction between a sensor and the badge of a patient or caregiver, or between the badge of a patient and the badge of a caregiver.

The controller is a microprocessor which executes predetermined or user modifiable software programs, stored in its internal memory, to collect activity data transmitted thereto from within the tracking environment and to process and store the activity data. In a preferred embodiment, a caregiver, such as a physician, interacts with the controller at the interface to select the type and extent of monitoring of activities performed for a specific patient. The controller determines and stores in its memory a time indexed record of the locations of patients and caregivers, patient-caregiver, patient-equipment and caregiver-equipment proximity information, and care events performed or occurring in connection with the patient, based on the collected activity data. Further, the controller makes information concerning the monitored activities and the status of the event schedule for the patient, which is based on assessment of the collected activity data, available in real time.

In a preferred embodiment, the controller collects and correlates data relative to whether a caregiver was in proximity to a patient for a predetermined time interval. In a further preferred embodiment, patient-caregiver proximity information is included in the identification data signals that the badge of a caregiver generates only after the caregiver badge is activated by a trigger signal transmitted by the badge of a patient or by a sensor located in a predetermined zone of the tracking environment. Thus, the controller assesses schedule status using activity data representative of caregiver location which is generated only when the caregiver is within the proximity of, for example in the same room as, the patient to whom the caregiver is assigned to provide care services, thereby avoiding pervasive tracking of caregivers.

BRIEF DESCRIPTION OF THE DRAWINGS

Other objects and advantages of the present invention will be apparent from the following detailed description of the presently preferred embodiments, which description should be considered in conjunction with the accompanying drawings in which.

DETAILED DESCRIPTION OF PREFERRED EMBODIMENTS

Figure 1:
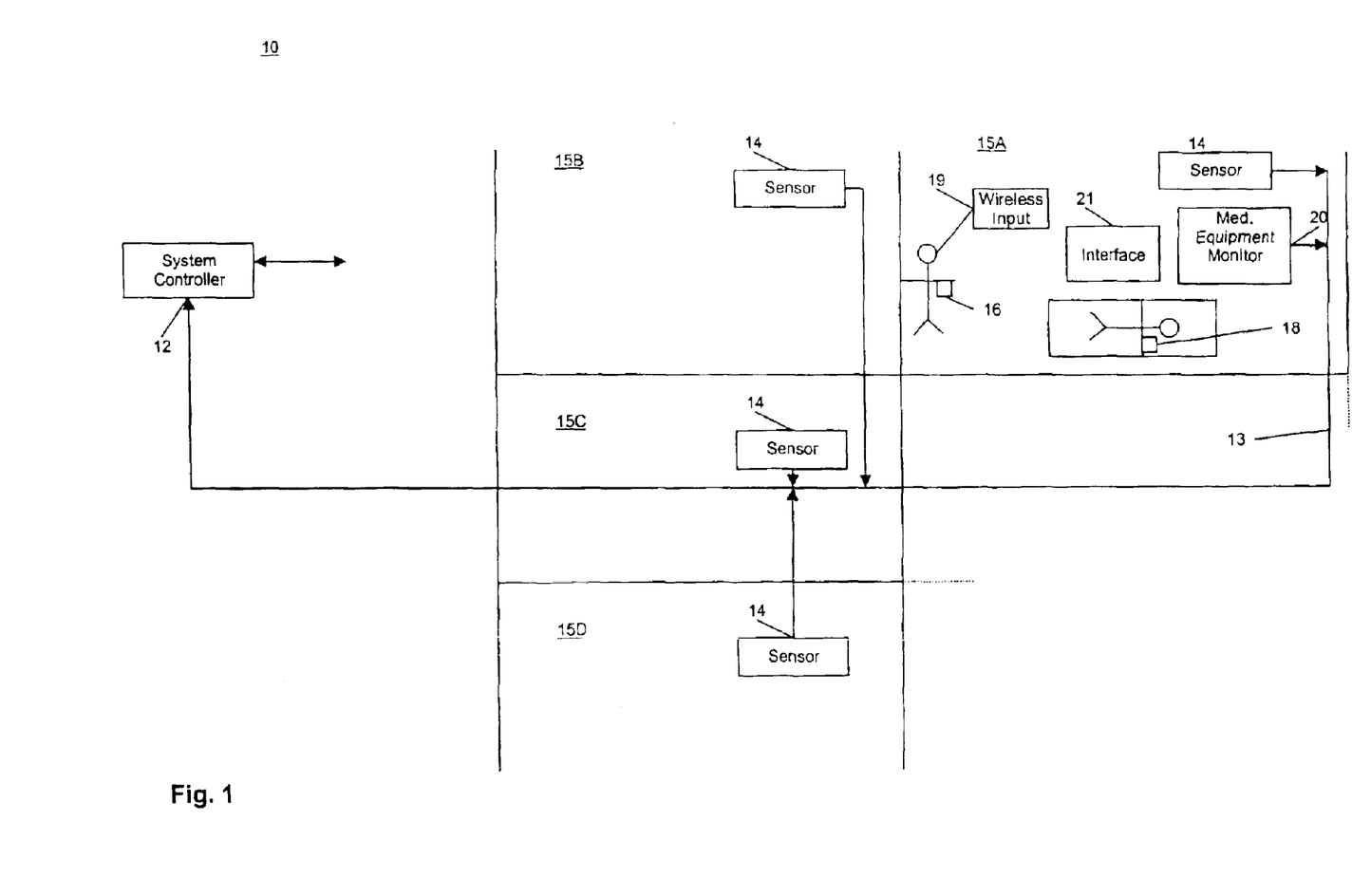
FIG. 1 is a block diagram of a system for collecting clinical activity data from within a tracking environment and processing the collected activity data in accordance with one embodiment of the invention.

FIG. 1 shows in block diagram form an embodiment of a system 10 for monitoring activities in a health care facility tracking environment in accordance with a preferred embodiment of the present invention. The system 10 is an automated, universal and electronic monitoring platform for a health care facility, which is a combination wired and wireless network and utilizes IR and RF based locating and positioning technologies and technical knowledge concerning physiologic measurements, to provide, preferably with real time data acquisition and information retrieval capability, evaluative information on the real time progress and performance of patient care and a record of caregiver, patient and medical equipment locations and medical treatment and operational process events performed or that occurred within the tracking environment. Although the present invention is described in detail below in connection with monitoring activities within a health care facility, it is to be understood that activities in other environments, such as in an industrial or commercial environment, can be monitored in accordance with the present invention to make information available in real time concerning the activities and performance of activities associated with an event schedule specific to those environments.

Referring to FIG. 1, the system 10 includes a controller 12 coupled by wired or wireless data communication links to sensors 14, a wireless, portable caregiver identification badge 16, a wireless, portable patient identification badge 18, a wireless, portable voice activity data transmitter 19, medical diagnostic monitoring equipment 20 and an interface 21. The components of the system 10, exclusive of or including the controller 12, are within a tracking environment to provide that the system 10 collects activity data, preferably passively, automatically and in real time, representative of medical treatment and operational process events occurring or performed within the tracking environment.

The badges 16 and 18 are active IR transceiver assemblies that automatically emit digitally encoded IR identification ("ID") data signals of predetermined amplitude which identify the source of the energy signal transmission. Alternatively, the badges 16 and 18 are RF or combination RF/IR transceiver assemblies which emit IR or IR and RF ID data signals, respectively, either automatically or when activated manually or upon detection of a trigger signal. In a further embodiment, a badge includes an IR scannable barcode or an RF transponder which when interrogated respectively by an IR or RF source, such as another badge or one of the sensors 14, reflects ID data signals preferably toward the interrogating source. See U.S. Pat. No. 6,154,139 and WO 01/33748, incorporated by reference herein.

The transmitter 19 is a conventional voice activated voice recognition device which detects and processes voice energy signals for generating corresponding voice data. The transmitter 19 further includes an RF or IR transmitter assembly for generating and transmitting digitally encoded RF or IR voice data signals based on the voice data.

Each of the sensors 14 includes a transceiver for transmitting RF or IR interrogating signals and receiving IR or RF identification data signals and voice data signals. Further, each sensor 14 includes a digital signal processing assembly and electrical or optical signal generating components for generating and transmitting digitally encoded activity data signals to the controller 12, based on the detected signals, over an electrical or optical fiber data communication link, or combination electrical and optical link, 13. The activity data signals are encoded to indicate time of their transmission from the sensor 14 and the detected location and identity of the caregiver, patient or the voice data transmitter 19 which is the source of the activity data. The sensors 14 are positioned at strategic locations or zones 15A, 15B, 15C, 15D, etc., within the hospital tracking environment, such as passageways, entry and/or exit points within a patient room, treatment rooms, single function rooms, above patient beds, etc., to permit accurate and complete real time tracking of the locations and movement of patients and caregivers and medical and diagnostic equipment.

In a preferred embodiment, the sensor 14 transmits RF or IR energy signals to interrogate a passive badge and processes the reflected interrogating energy signals, which constitute encoded identification data signals, to generate activity data representative of the location and identity of the badge interrogated. In a further embodiment, the sensor 14 detects and processes interrogating energy signals, whose source is another badge and which have been reflected by a passive badge, to generate activity data representative of the location of the interrogated badge. In still a further embodiment, the reflected interrogating signal includes data encoding which identifies the badge that is the source of the interrogating signal, and the sensor includes such source identification data in the activity data transmitted to the controller.

In a preferred embodiment, the caregiver badge 16 includes digital signal processing components, similar to those included in a sensor 14, and transmits RF or IR interrogating energy signals to interrogate a passive badge 18. The caregiver badge 16 receives and then processes the reflected interrogating energy signals to generate activity data, and stores the activity data in its memory. The badge 16 transfers the activity data to the system 10 by, for example, wireless coupling of the badge 16 to an interface 21, which provides for automatic data transfer between the badge 16 and the interface 21.

In a further preferred embodiment of the system 10, the caregiver badge 16 is an IR transceiver that is normally in an inactive or non-transmitting state. (It is noted that the badge may nevertheless transmit periodic signals on a relatively infrequent basis, in order to confirm functionality, but not so often as to interfere with the privacy protection protection feature relative to the normal inactive or non-transmitting state). The badge 16 may include a manual pushbutton trigger which, when depressed, activates the badge 16 to cause the badge 16 to transmit IR identification data signals. In addition, the badge 16 includes IR signal detection components which, upon receipt of an IR trigger signal that is transmitted at least at a predetermined minimum power level and/or from within a predetermined signal detection radius of the badge 16, or from an encoded signal which is preprogrammed to trigger the badge, activate the badge 16 to cause transmission of IR identification data signals. The badge 18 continuously transmits IR trigger signals having a sufficient power level for activating the badge 16. When the badge 18 is located within IR detection radius and also within the line of sight of the badge 16, the badge 16 is activated. In a further embodiment, the activated badge 16 transmits IR identification data signals only for a predetermined interval, after which it ceases to transmit the identification data signals unless another triggering event occurs. In an alternative preferred embodiment, selected sensors 14 also transmit IR trigger signals. Referring to FIG. 1, if the badge 18 activates the badge 16 in the zone 15A, the sensor 14 in the zone 15A detects the identification data signals from the activated badge 16 and, hence, generates activity data representative of a proximity condition between a caregiver and patient in the zone 15A at a specific time.

In an alternate embodiment which may or may not operate in conjunction with the triggering based mechanism set forth above, the system 10 does not collect information concerning caregiver location if a proximity condition between a caregiver and a patient does not exist. Thus, information concerning caregiver location which is unrelated to patient care is not monitored, thereby protecting the privacy interests of caregivers. For example, signals generated by a caregiver badge are received by the sensors, but the microprocessor is programmed to ignore, i.e. not record location data for these signals, unless certain criteria are met. Such criteria should be indicative of a relevant activity, such as tending to a patient for which that caregiver is assigned, or entering an assessment room relative to that caregiver's specialty (such criteria being accessible by the microprocessor).

In a further preferred embodiment of the system 10, the badges 16 and 18 are RF based devices that utilize short distance wireless transmission technologies, such as LAN and Bluetooth, and operate to generate caregiver-patient proximity information. For example, the badge 16 is activated to transmit RF identification signals for receipt by a sensor, which is located within a predetermined distance of both the caregiver badge 16 and a patient badge 18, when the badge 18 is within the RF detection of radius of the badge 16 and the badge 16 receives RF trigger signals transmitted at least at a predetermined power level by the badge 18. The use of RF based signals to detect a proximity condition avoids potential problems associated with the use of IR, line of sight based techniques. IR signal based detection often does not detect a proximity condition, such as, for example, if physical obstructions are between the badges 16 and 18 which are otherwise within a few feet from each other in a room.

In a further embodiment, the badge 16 is an IR reader that transmits IR interrogating signals toward the badge 18 of a patient which includes an IR readable barcode. The barcode of the badge 18 reflects the interrogating signals to generate IR identification data signals, preferably indicating the identity of the interrogating badge 16 and the interrogated badge 18. The sensor 14 detects the IR ID signals and then routes to the controller 12 activity data signals which indicate a proximity condition was detected for the badges 16 and 18 at the zone of the sensor 14.

It should be clear that the any number of possible wireless technologies may be employed in order to achieve the object of the invention. The aim is allowing caregivers (or other personnel desiring a degree of privacy) to move about the facility without constant monitoring, while also permitting such monitoring selectively when it becomes relevant and necessary. By setting up the caregiver badges to remain dormant, until activated by a triggering event, this aim may be achieved. The triggering event may be anything which is linked to the concept of 'relevance', such as receiving a signal of a certain strength, or of a certain type, from a certain type of transceiver associated with a particular type of person or equipment. The event may also be such that any signals will trigger activation within a particular time frame, or particular location within a facility. Relevance may also be made more specific, such that in addition to being linked to a particular type of person, such as a patient badge, the trigger is dependent on a predetermined linkage, such as where it will only activate in relation to specific patients, or only upon a correlation with a predetermined scheduled event (i.e. surgeon is scheduled to be in surgery theater at a certain time, and badge will be activated by signals received at that place and time). Thus, it should be seen that the system can be set up to achieve these aims through a variety of available or future wireless technologies, sensors, badges, transceivers, all linked by a network to a microprocessor. The specific examples using particular types of equipment should be seen as non-limiting.

Furthermore, the aim of the invention can also be achieved by using the triggering criteria, such as preprogrammed linking of each caregiver with certain patients, certain types of equipment, certain wards, and/or linking by expected attendance at scheduled events. Rather than relying on the triggering of a caregiver badge to an activated state, the system may use standard tracking arrangements based on continually active transmitters for all personnel. The microprocessor evaluates the relevancy of the transmitted caregiver signal. If the signal is not correlated to a proper patient or ward, or an expected scheduled event, for example, the signal is not recorded as a location data point.

The medical monitoring equipment 20 includes a physiological data collection assembly, such as a conventional digital signal processor and a memory. The assembly is coupled to the data output port of medical equipment (not shown), or an existing hard wired data network to which the data port of the medical equipment is connected. The assembly detects available identification data, which identifies the patient, caregiver and equipment, and physiological output data, such as digital data representative of blood oxygen level provided at an output port of a pulse oximeter. The assembly then converts the detected data to time encoded digital activity data signals which include the physiological data and identify the caregiver, the medical equipment and the patient associated with the physiological data. The equipment 20 further includes a transmitter assembly which transmits the digital activity data signals to the controller 12, in substantially real time, over the link 13 which extends between the equipment 20 and the controller 12.

The interface 21 preferably is a microprocessor based graphical display, such as a flat screen monitor, including an input device, such as a keypad or a keyboard. The interface 21 includes a RF transceiver assembly which transmits to the controller 12 digitally encoded RF activity data signals, based on data that a caregiver enters concerning a care event, for example, data indicating that the caregiver administered medication to the patient at a particular time. The interface 21 furthermore receives RF control signals transmitted from the controller 12 and instructing the interface 21 to, for example, display text data or cause an attached or an integrated annunciator or light source to sound or illuminate, respectively. In a preferred embodiment, the interface 21 is a PDA or keypad-based data entry device including a IR barcode scanner or a smart card reader. In an alternative preferred embodiment, the interface 21 is coupled to a wired LAN to which all components of the system 10, except for caregiver and patient badges, are coupled.

In a preferred embodiment, the system 10 is a completely wireless network encompassing an entire hospital facility and monitors physiologic measurements of a patient continuously, regardless of location, and also the locations of the patients and caregivers from ID data signals generated by RF or IF energy signal interaction between a sensor and a badge or between a patient badge and a caregiver badge.

Figure 2:
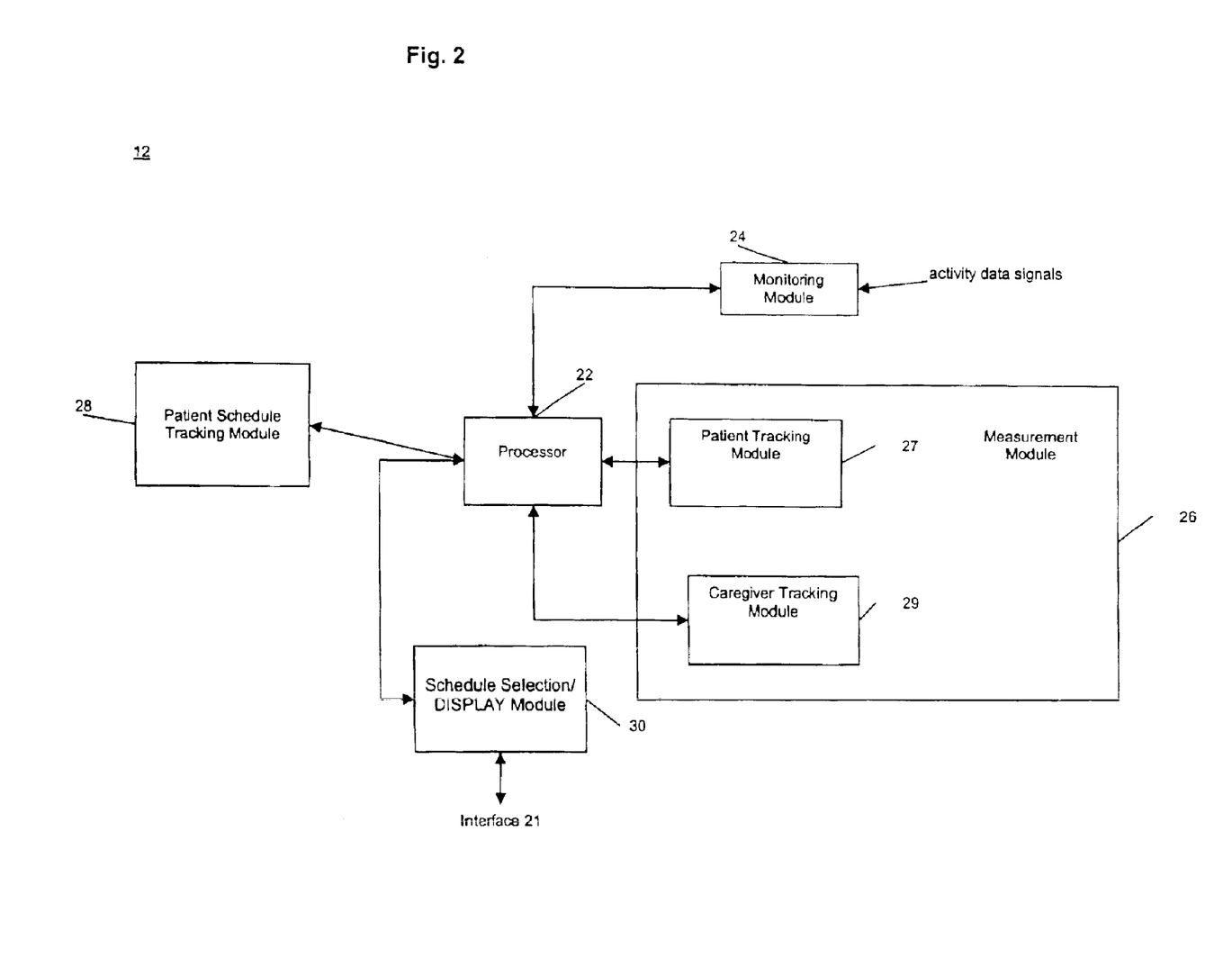
FIG. 2 is a block diagram of the controller of the system of FIG. 1.

Referring to FIG. 2, the controller 12 includes modules that execute software programs to implement the features of monitoring activities in a health care facility tracking environment in accordance with the present invention. It is to be understood that each of the modules within the controller 12 which is described below as performing data processing operations is a software module or, alternatively, a hardware module or a combined hardware/software module. In addition, each of the modules of the controller 12 suitably contains a memory storage area, such as RAM, for storage of data and instructions for performing processing operations in accordance with the present invention. Alternatively, instructions for performing processing operations can be stored in hardware in one or more of the modules in the controller 12.

In accordance with a preferred embodiment, the system 10 collects activity data, preferably passively, automatically and in real time, relating to patient and caregiver locations and proximity and events and measurements performed or occurring which are associated with a patient care event schedule including clinical care pathway events, and generates from the collected activity data a substantially complete and continuously updated record of patient care that is accessible in real time.

Referring to FIG. 2, the controller 12 includes a processor module 22 coupled to a monitoring module 24, a measurement module 26, a patient schedule tracking module 28 and a schedule selection/display module 30.

The monitoring module 24 includes a receiver assembly for receiving digitally encoded activity data signals which are carried on electrical or optical signals conveyed over suitable wired data communication links extending between the controller 12 and the source of the signals, such as the monitoring equipment 20 and the sensors 14. Further, the receiver assembly can receive RF and IR activity data signals transmitted from the tracking environment. The module 24 extracts the activity data from the carrier signals and then forwards the activity data to the processor 22. The processor 22, based on the source and location identification information encoded with the activity data, selectively routes the activity data associated with patient or caregiver badges respectively to a patient tracking module 27 or a caregiver tracking module 29 in the measurement module 26. The modules 27 and 29 respectively process the received activity data to create a time indexed record of patient and caregiver location within the hospital tracking environment and store such indexed records in their respective memories. In a preferred embodiment, the modules 27 or 29 determine the locations of a patient and caregiver based on the identities of the sensors that are the sources of the activity data signal transmissions, or by using triangulation and/or other multilateration identification techniques.

In a further preferred embodiment, the module 29 stores records of caregiver location for a specific caregiver only if the module 29 determines from the activity data that the caregiver was detected as being in proximity for a predetermined time interval with a patient for which the caregiver was assigned to care. For example, a caregiver can be deemed to be in proximity with the patient to be cared for by the caregiver if the caregiver and patient are simultaneously present in the same zone within the tracking environment for a predetermined time interval.

In another preferred embodiment, the module 29 includes caregiver location information which is based upon identification data signals that were generated only when a proximity condition between the caregiver and a patient existed. The stored proximity information for the caregiver preferably is indexed by the patient to which the caregiver is assigned. The proximity information preferably is obtained based on interaction between the respective badges of the caregiver and patient where the patient badge triggers the caregiver badge to generate identification signals which also identify the triggering patient source. As discussed below, the module 28 can use this proximity information to deduce that actions in the event schedule have been performed, and then seek a confirmation to ascertain whether the conclusion is proper.

In addition, the processor 22 recognizes activity data whose sources are the equipment 20 and the transmitter 19 and routes such activity data to the measurement module 26. The module 26 processes and then stores in its memory such activity data in the form of a record indexed by source and time and cross-referenced by patient and caregiver, as suitable and available. As part of the processing, the module 26 converts the activity data representative of voice data into a data form suitable for storage, retrieval and processing by the other modules of the controller 12.

Referring again to FIG. 2, the module 30 includes a transceiver assembly, preferably having RF, optical or electrical signal reception and transmission capability, which facilitates exchange of data between the controller 12 and the interface 21. For example, the module 30 can route control data signals to the interface 21 which cause the interface 21 to sound an alarm or display a prompt on its screen requesting additional information from a caregiver. Also, the module 30 can receive from the interface 21 activity data and instructions concerning details of the schedule to be applied to a particular patient.

The module 28 includes in its memory predetermined software programs which constitute patient event schedules. A caregiver, such as a physician, at the interface 21 selects or modifies an existing schedule for a particular patient. The module 28 performs a selected program to effectuate, in accordance with the selected patient schedule, the continuous evaluation of whether events scheduled have been performed, need to be performed, etc. The module 28 executes the programs by having the processor 22 retrieve time indexed location records of patients and caregivers, patient-caregiver proximity and other patient specific activity data from the modules 26, 27 and 29, as suitable.

Figure 3:
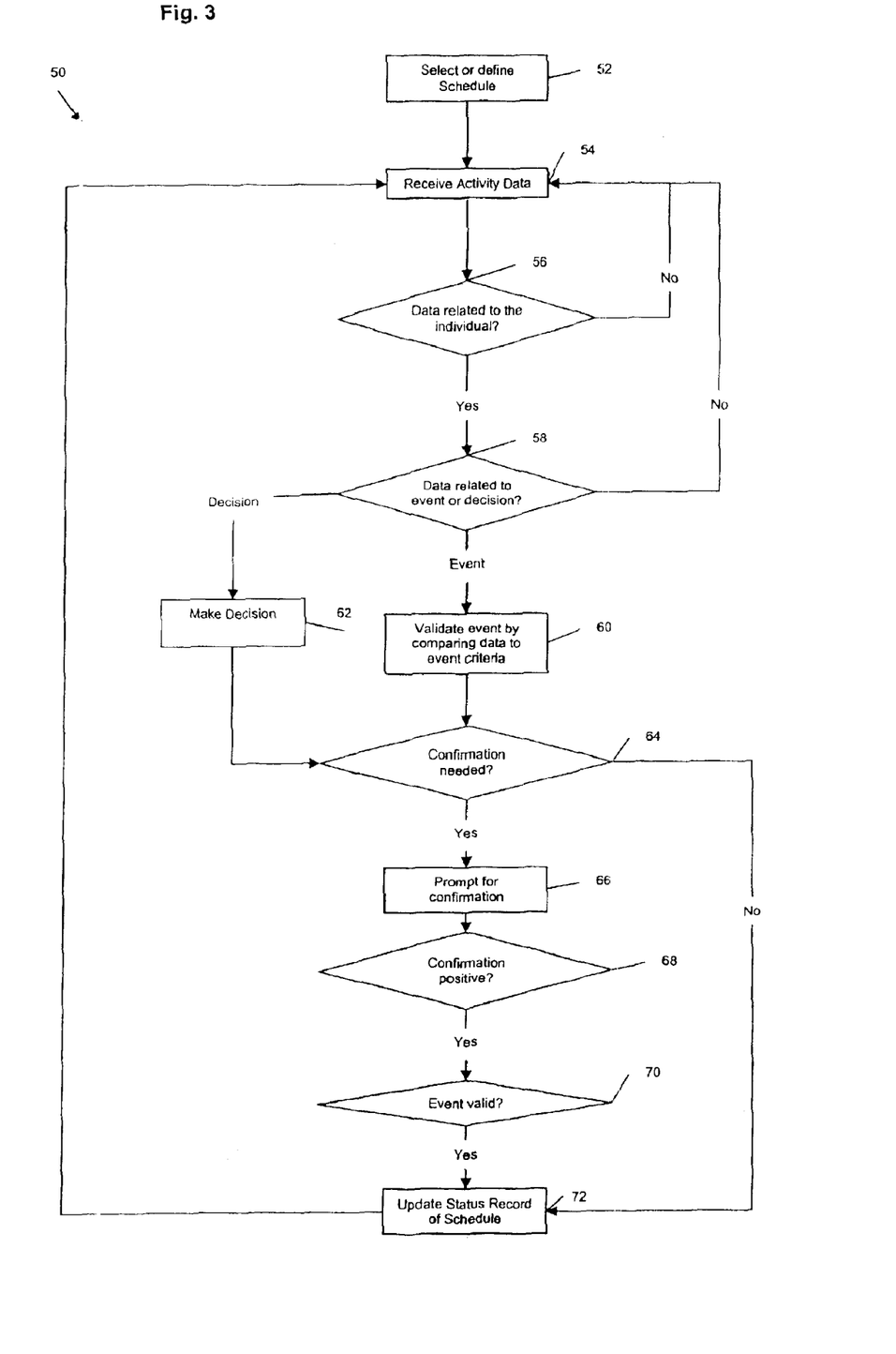
FIG. 3 is a flowchart of an implementation of the processing of activity data collected by the system of FIG. 1 in relation to a care path event schedule.

Referring to FIG. 3, the system 10 in a preferred embodiment implements steps of an exemplary process 50 that facilitates real time evaluation of a patient event schedule in a hospital environment and documentation of activities relevant to the schedule and hospital operational processes in general. Referring to FIGS. 2 and 3, the module 28 retrieves, via the processor 22, time indexed records concerning patient and associated caregiver location and patient-caregiver proximity from the respective modules 27 and 29 and physiological measurement information from the module 26. These records are derived from and representative of the ID data signals generated by or at the badges 16 and 18, the voice data signals transmitted by the transmitter 19 and the activity data signals transmitted by the equipment 20, as suitable. The module 28, based on the event schedule and associated event criteria, evaluates the recorded data and in real time interprets the activity data in the context of the events of the schedule. The module 28 updates the status of performance of the schedule based on the evaluations that are made.

In step 54, the monitoring module 24 continuously receives activity data signals from the tracking environment, extracts the activity data and then forwards the extracted activity data to the processor 22. For example, when the physician with the badge 16 moves the admitted patient with the badge 18 to the diagnosis room designated zone 15A, the normally off RF signal based caregiver badge 16 is activated when the badge 16 is within at least ten feet of the patient badge 18. The badge 18 continuously transmits RF trigger signals at a power level that the badge 16 can detect when the badge 18 is within a ten foot radius of the badge 16. Consequently, the activated badge 16 generates RF identification data signals that the sensor 14 in the zone 15A detects. The sensor 14, in turn, generates and transmits activity data signals indicating that the physician and patient assigned to the badges 16 and 18 respectively were detected as being in proximity in the zone 15A at certain times. The proximity information continues to be generated and transmitted to the module 24 while the physician performs an EKG that is monitored by the monitor 20. The monitor 20 transmits activity data signals, preferably including physician and patient identification information as well as EKG vital sign information, having the same time stamp information as the proximity information that the sensor 14 in the zone 15A transmits concerning the physician and patient being detected as present simultaneously in the zone 15A. When the physician leaves the room 15A and walks more than ten feet away from the patient while the patient remains in the room 15A, the sensor 14 in the room 15A no longer transmits the proximity information.

As part of step 54, the processor 22 suitably routes the activity data to the measurement module 26, and its modules 27 and 29. The modules 26, 27 and 29, in turn, process the activity data to generate records indexed by time, patient, caregiver, patient and caregiver locations and proximity, as applicable, and store such indexed data in memory.

In a preferred embodiment where the sensors 12 passively and automatically collect information concerning the locations of patients and caregivers and care events performed or associated with patients, an irrefutable, electronic record of patient care is created. The record is not open to question because human judgment or action, such as manual marking a time entry on a clipboard or entering of a time in a computer, is absent. This form of monitoring of activities improves utilization of resources and also assists in the process of credentialing a health care facility.

Other modules in the controller 12, such as the modules 28 or 30, advantageously can access the data records stored in the module 26, which includes the modules 27 and 29, in real time.

In a preferred embodiment, the processor 22 can retrieve and process the records stored in the module 26 offline, in other words not in real time, to generate prepared reports relating to, for example, patient charting, order entry, outcome management, quality assessment, utilization review and patient admission details, such as patient tracking, bed management and scheduling. For example, the processor 22 can use the activity data to generate a prompt for an automated billing system which states the following: "Dr. Smith, pulmonologist, was in proximity to Patient Jones, respiratory failure, for 37 minutes today starting at 09:32. Was this a billable pulmonary consult?"

In step 56, the processor 22 continuously retrieves and evaluates the records stored in the module 26 to determine whether new activity data related to the individual patient has been recorded. If yes, the processor 22 forwards the identified new data records to the module 28.

In a preferred embodiment, the processor 22 effectively filters the collected records concerning a particular patient by forwarding to the module 28 only new data records concerning caregivers who were detected as being in proximity with the patient and also designated as potential caregivers for the patient in accordance with the care event schedule for the patient. Thus, the module 28 evaluates and processes only that activity data received from the tracking environment which are relevant to the predetermined schedule selected for the individual patient. The processor 22 does not forward to the module 28 activity data received at the module 24 and stored in the module 26 which is not relevant to the particular patient and patient schedule, such as the casual presence of a podiatric caregiver in the vicinity of a patient scheduled for open heart surgery during transfer of the patient to an operating room.

In step 58, the module 28 determines whether the recorded activity data that the processor 22 forwarded relates to an event or a decision in the schedule. For example, an event can include the taking of vital signs, which the triage nurse records at an interface 21; the patient leaving a waiting area, which the system 10 passively detects and records; a nurse seeing the patient, which the nurse records by pushing an alarm button on the patient badge 18; a physician seeing the patient, which is recorded when the sensor 14 detects the physician as present in the patient's room 15A and when the physician confirms the meeting and the diagnosis at the interface 21 after being prompted; drawing of the patient's blood sample in a laboratory, which is recorded based on patient location detection and the laboratory nurse scanning the patient badge 16 with an RF reader coupled to the interface 21; and a nurse dispensing medication prescribed by the physician to the patient, which the nurse records at the interface 21 by scanning the badge 16 and a badge including a barcode attached to a medicine vial.

If the module 28 determines that the recorded data corresponds to an event set forth in the schedule, the module 28 in step 60 validates the determination by comparing the activity data associated with the event with criteria for confirming that the event indeed occurred. In a preferred embodiment, the system 10 validates an event using caregiver-patient proximity information stored in the module 29. For example, a specific event can be validated if the proximity information indicated that a selected caregiver was detected as being within a predetermined distance from the patient for whom the caregiver is designated to provide care at specified times.

The proximity information used in step 60, in a preferred embodiment, is based on activity data obtained using RF and/or IF location technologies that identify the precise locations of the patient and caregiver. For example, in step 58 the module 28 may have determined the presence of the scheduled event of measurement of the patient's EKG based on the EKG vital sign information, which is indexed with the patient's name and was transmitted by the monitoring equipment 20. The schedule requires that proximity information be used to validate that the EKG was performed. Therefore, in step 60, the module 28 retrieves and evaluates the proximity data for the patient to confirm that the EKG measurement event was performed for the patient. For example, the module 28 evaluates the proximity information to determine whether the EKG vital sign information was transmitted at substantially the same time that the physician and patient were in proximity in the room from which the EKG vital sign information was transmitted.

In an alternative embodiment, the module 28, from the patient location records stored in the module 26, validates the EKG event for the patient by ascertaining whether the patient had been to a particular diagnostic room in the hospital, stayed there for a believable length of time and then had left. The patient location record is derived from, for example, activity data that a sensor positioned at the entrance to the diagnostic room generates by scanning a scannable IR barcode identifier badge attached to the patient's wrist or to a movable gurney. The module 28 then processes this information and concludes, without human intervention, or at least subsequently prompts for human confirmation at the interface 21, that a procedure associated with the room, namely, the EKG measurement, which was indicated as the next step on the care schedule that had not yet been performed, had been completed.

If the module 28 in step 58 determines that the recorded data relates to a decision, the module 28 in step 62 assesses the recorded data to decide, for example, whether the schedule should be updated. For example, the decision criteria relating to an event in the schedule may require the module 28 to continuously evaluate information concerning several vital signs of the patient, such as blood pressure, blood oxygen level and heart rate. If the vital signs fall within undesirable ranges established by the schedule criteria, the module 28 would update the schedule such that data obtained in connection with the event is reported when the schedule status is accessed.

In step 64, the module 28 determines whether the schedule requires that a decision made or an event validated by the module 28 based on specific recorded data must be confirmed using other data. If the schedule requires a confirmation, the module 28 in step 66 transmits a control signal to the display module 30, which in turn causes generation of a confirmation prompt at the interface 21. The prompt requests the caregiver to confirm, for example, the decision by the module 28 that the patient's medical vital signs have improved sufficiently, such that the dosages and types of medication to be provided can be changed to new values. Based on the caregiver's response, which would be limited to a "Yes" or "No", the module 28 in step 68 determines whether the confirmation was positive.

If the confirmation is positive in step 68, the module 28 in step 70 determines if a detected event was valid. For example, if the module 28 determines that the event of a caregiver performing an EKG had occurred, based on recorded physiological measurement data which the monitoring equipment 20 coupled to the EKG diagnostic equipment transmitted to the controller 12, the module 28 assesses the caregiver and patient location record or proximity information to confirm the event. The event confirmation criteria, for example, require that the recorded data establish that the caregiver and patient were in the same zone during the time when the EKG procedure normally should have been preformed.

If the event is validated in step 70, the module 28 in step 72 updates the status record for the event schedule. For example, the module 28 updates the record of the schedule to indicate that a specific caregiver performed the EKG at a specified time, the results of the EKG and when a caregiver analysis of the EKG results became available for review. Once the module 28 updates the schedule status, the schedule and details on its status are available for display at the interface 21. Further, the module 28 henceforth processes the recorded data in accordance with the updated schedule requirements.

The caregiver thus can access in real time the status of the event schedule for the patient, which has been updated based on an evaluation of events that have occurred and the procedures performed or to be performed. From the available information, the caregiver can determine, for example, the expected and actual time frame for a particular episode of care, the tasks that must be and were performed at different times during that episode of care and the expected and actual outcomes at different stages of the patient's recovery.

In an alternative preferred embodiment, the activity data stored by the system concerning caregiver location patterns can be accessed to permit iterative and quick changes in patient schedules. For example, the electronic care record can indicate that nurses are spending a lot of time off the unit, such as on intrahospital patient transport, which information is valuable for assessing the care processes and resource utilization. At the interface 21, the caregiver, with relative ease, provides instructions to the controller 12 to achieve rapid implementation of a revised schedule, to check the results of the revised schedule and to continue to fine tune the schedule iteratively.

Although preferred embodiments of the present invention have been described and illustrated, it will be apparent to those skilled in the art that various modifications may be made without departing from the principles of the invention.

What is claimed is:

1. A method for electronic monitoring of activities in a tracking environment comprising:

selecting a schedule including a plurality of events;

collecting activity data in substantially teal time from the tracking environment, wherein the activity data includes proximity information concerning first and second energy signal identification badges, wherein the first badge is a normally off energy transceiver, wherein the first badge is activated when the first badge detects trigger signals transmitted at a minimum power level and from within a predetermined radius of the first badge, wherein the second badge generates the trigger signals for activating the first badge, and wherein the first badge generates activity data signals representative of a proximity condition between the first and second badges when the first badge is activated by the trigger signals from the second badge;

evaluating the activity data in substantially real time to determine whether at least one of the events of the schedule has been performed, wherein the evaluating includes using the proximity information;

updating a status record of the schedule in substantially real time based on the evaluation of the activity data; and making the status record of the schedule and the activity data available for access in real time.

2. A method for selectively monitoring location of a service provider within a tracking environment comprising:

providing each of a monitoree and a service provider with an energy signal identification badge;

providing an energy signal transceiver at a predetermined zone within the tracking environment or to at least one of the service provider and the monitoree;

determining whether the monitoree is within a proximity of the service provider based on energy signals received at the transceiver and generated at or reflected away from the badge of at least one of the service provider and the monitoree, wherein the energy signals represent detection of the presence of the service provider at a location at a first time; and storing data representative of the detection of the service provider at the location at the first time only upon determination that the service provider was within the proximity of the monitoree at the first time.

3. The method of claim 2, wherein the service provider badge is normally of and activated by a trigger signal, and wherein, when the monitoree badge transmits a trigger signal for activating the normally off badge of the service provider, the service provider badge transmits data signals indicating a proximity condition between the service provider and the monitoree.

4. A system for selectively collecting location information in a tracking environment, comprising:

a first energy signal identification badge for detecting trigger signals and transmitting identification data signals indicating existence of a proximity condition between the first badge and a source of the trigger signals;

wherein the trigger source transmits trigger signals of a predetermined power level, wherein the first badge can detect the trigger signals only if the first badge is within a predetermined radius of the trigger source when the trigger source transmits the trigger signals; and wherein the first badge transmits the identification data signals when the first badge detects the trigger signals transmitted by the trigger source.

5. The system of claim 4, wherein the trigger signals and the identification data signals are at least one of radio frequency and infrared energy signals.

6. The system of claim 4, wherein the trigger source is a second, portable identification badge.

7. The system of claim 4, wherein the trigger source is a fixed sensor transceiver assembly for detecting the identification data signals.

8. The system of claim 4, wherein the trigger source is a fixed energy signal identification badge.

9. The system of claim 4, wherein the first badge is a source of pre-trigger signals, wherein the pre-trigger signals are converted to trigger signals when reflected by an encoded energy reflecting medium.

10. The system of claim 4, wherein the reflecting medium is an RF transponder or IR readable bar code.

11. A system for electronic monitoring of activities in a tracking environment comprising:

a plurality of energy identification badges disposed in the tracking environment for generating identification data signals;

a plurality of sensors disposed in the tracking environment for detecting the identification data signals, converting the detected signals into activity data signals and transmitting the activity data signals, wherein the detecting, converting and transmitting are performed by the sensors in substantially real time;

a microcontroller for receiving the activity data signals and processing the activity data in accordance with a schedule including a plurality of events, wherein the processing is in real time and comprises:

evaluating the activity data to determine whether at least one of the events of the schedule has been performed, wherein the activity data includes proximity information concerning first and second energy signal identification badges, wherein the evaluating includes using the proximity information, wherein the first badge is a normally off energy transceiver, wherein the first badge is activated when the first badge detects trigger signals transmitted at least at a predetermined minimum power level and from within a predetermined radius of the first badge, wherein the second badge generates the trigger signals for activating the first badge, and wherein the first badge generates activity data signals representative of a proximity condition between the first and second badges when the first badge is activated by the trigger signals from the second badge;

updating a status record of the schedule based on the evaluation of the activity data; and making the status record of the schedule and the activity data available for access in real time.

12. The system of claim 11, wherein at least one of the badges automatically generates identification data signals and the sensors passively and automatically detect the identification data signals.

13. The system of claim 11, wherein at least one of the sensors passively and automatically causes at least one of the badges to generate identification data signals.

14. The system of claim 11, wherein at least a first of the badges passively and automatically causes at least a second of the badges to generate identification data signals and wherein the sensors passively and automatically detect the identification data signals.

15. A method for selectively recording location information in a tracking environment, comprising:

receiving transmitted signals indicative of a particular source and location, determining whether said source and location correlates to an expected relationship, and if the determination is positive, recording information relative to the source, location and time of the signal, and if the determination is negative, insuring that information relative to the source, location and time of the signal is not recorded.

16. A system for selectively recording location information in a tracking environment, comprising:

means for transmitting signals indicative of a first source and its location, sensors for receiving transmitted signals, means for communicating the received signals to a controller, means for determining whether the source and location correspond to an expected relationship, means for recording the source, location and time of the signal if the determination is positive, and for insuring that the source, location and time of the signal is not recorded if the determination is negative.

17. The system of claim 16, further comprising means for transmitting signals indicative of a second source, wherein the source, location and time of the signal are always recorded.

* * * * *

UNITED STATES PATENT AND TRADEMARK OFFICE
CERTIFICATE OF CORRECTION

PATENT NO. : 6,954,148 B2
DATED : October 11, 2005
INVENTOR(S) : Pulkkinen et al.

It is certified that error appears in the above-identified patent and that said Letters Patent is hereby corrected as shown below:

<u>Column 10,</u>
Line 7, delete "that the any number" and insert -- that any number --.

<u>Column 15,</u>
Lines 66-67, delete "have been preformed" and insert -- have been performed --.

<u>Column 16,</u>
Line 41, delete "substantially teal time" and insert -- substantially real time --.

Signed and Sealed this

Eleventh Day of April, 2006

JON W. DUDAS
*Director of the United States Patent and Trademark Office*